US011181523B2

(12) United States Patent
Toro-Cabrera et al.

(10) Patent No.: US 11,181,523 B2
(45) Date of Patent: Nov. 23, 2021

(54) METHOD FOR THE EARLY DETECTION OF ACUTE KIDNEY INJURY IN CRITICAL PATIENTS, USING FIBROBLAST GROWTH FACTOR 23, KLOTHO AND ERYTHROPOIETIN AS BIOMARKERS

(71) Applicant: Universidad De Chile, Santiago (CL)

(72) Inventors: Luis Alejandro Toro-Cabrera, Santiago (CL); Luis Fernando Michea-Acevedo, Santiago (CL)

(73) Assignee: UNIVERSIDAD DE CHILE, Santiago (CL)

(*) Notice: Subject to any disclaimer, the term of this patent is extended or adjusted under 35 U.S.C. 154(b) by 579 days.

(21) Appl. No.: 15/767,708

(22) PCT Filed: Oct. 14, 2016

(86) PCT No.: PCT/CL2016/050056
§ 371 (c)(1),
(2) Date: Apr. 12, 2018

(87) PCT Pub. No.: WO2017/063100
PCT Pub. Date: Apr. 20, 2017

(65) Prior Publication Data
US 2018/0289306 A1 Oct. 11, 2018

(30) Foreign Application Priority Data
Oct. 15, 2015 (CL) .................. 3047-2015

(51) Int. Cl.
G01N 33/573 (2006.01)
G01N 33/74 (2006.01)
G01N 33/493 (2006.01)
G01N 33/50 (2006.01)

(52) U.S. Cl.
CPC ......... G01N 33/573 (2013.01); G01N 33/493 (2013.01); G01N 33/5038 (2013.01); G01N 33/5091 (2013.01); G01N 33/746 (2013.01); G01N 2333/50 (2013.01); G01N 2800/347 (2013.01); G01N 2800/56 (2013.01); G01N 2800/60 (2013.01)

(58) Field of Classification Search
None
See application file for complete search history.

(56) References Cited

U.S. PATENT DOCUMENTS

| 2003/0119910 A1* | 6/2003 | Kamiya | A23L 33/15 514/564 |
| 2005/0048058 A1* | 3/2005 | Yamazaki | A61P 17/04 424/155.1 |
| 2005/0272101 A1 | 3/2005 | Devarajan | |
| 2010/0204189 A1* | 8/2010 | Petkovich | A61K 9/0053 514/167 |
| 2011/0045511 A1* | 2/2011 | Graus Porta | G01N 33/6872 435/7.92 |
| 2011/0059537 A1 | 3/2011 | Liangos | |
| 2011/0065136 A1* | 3/2011 | Labrie | G01N 33/566 435/15 |
| 2011/0135657 A1* | 6/2011 | Hu | A61P 43/00 424/158.1 |

(Continued)

FOREIGN PATENT DOCUMENTS

WO WO2010048347 6/2010
WO WO2010091231 8/2010

(Continued)

OTHER PUBLICATIONS

Pavic et al., "Secreted Klotho and FGF23 in chronic kidney disease Stage 1 to 5: a sequence suggested from a cross-sectional study", Nephrol Dial Transplant (2013) 28: 352-359 doi: 10.1093/ndt/gfs460 (Year: 2013).*
Hrubec et al., "Plasma Versus Serum: Specific Differences in Biochemical Analyte Values" Journal of Avian Medicine and Surgery 16(2):101-105, 2002 (Year: 2002).*
J Am Soc Nephrol. May 2011;22(5):810-20. doi: 10.1681/ASN.2010080796. Epub Apr. 14, 2011. Biological markers of acute kidney injury. Siew ED1, Ware LB, Ikizler TA.
Rev Med Chil. Sep. 2015;143(9):1114-20. doi: 10.4067/S0034-98872015000900003. [Incidence and consequences of acute kidney injury among patients admitted to critical care units], Boltansky A, Bassa C, Melani S, Sepúlveda A, Maldonado I, Postigo J, Sotta E, Vidueira P, Cavagnaro C, Cavada G, Benavente C, Villamizar G, Vukusich A, Irarrázabal CE.

(Continued)

Primary Examiner — Ellen J Marcsisin
(74) Attorney, Agent, or Firm — Procopio, Cory, Hargreaves & Savitch LLP

(57) ABSTRACT

The invention is an ex vivo method for early detection of acute kidney injury in critical patients, which includes the measurements of fibroblast growth factor 23 (FGF23), klotho (KL) and erythropoietin (EPO) as biomarkers. These measurements are obtained from a venous blood sample or urine, and allow the determination of the following indicators: 1=([FGF23]p×[EPO]p); 2=([FGF23]p/[Klotho]p); 3=([EPO]p/[Klotho]p); 4=([FGF23]p×[EPO]p)/[Klotho]p); where [X]p is defined as the plasma level of a specific molecule (X) which includes fibroblast growth factor 23 (FGF23), klotho (KL) or erythropoietin (EPO). If the value of the indicator 1, 2, 3, 4 or two or more thereof, is equal or higher than a cut-off point (10 U), the indicator and/or indicators allow the identification of patients with high risk of developing AKI, with a high sensitivity/specificity. Therefore high levels of the indicator are associated to a high probability of the presence/development of AKI, which allows to perform specific clinical interventions for patients with AKI. If the value of the indicator 1, 2, 3, 4 or two or more thereof, is lower than the previously mentioned cut-off point, the probability of presence/development of AKI is low, therefore patients require only standard treatment.

2 Claims, 6 Drawing Sheets

(56) References Cited

U.S. PATENT DOCUMENTS

| | | | | |
|---|---|---|---|---|
| 2012/0129857 | A1* | 5/2012 | Militzer | A61K 31/5377 |
| | | | | 514/236.2 |
| 2012/0232024 | A1* | 9/2012 | Breyer | A61K 38/17 |
| | | | | 514/21.2 |
| 2014/0017702 | A1 | 1/2014 | Mayer | |
| 2014/0038203 | A1 | 2/2014 | Arthur | |
| 2014/0178335 | A1* | 6/2014 | Basile | C07K 14/55 |
| | | | | 424/85.2 |
| 2015/0299193 | A1* | 10/2015 | Desai | C07D 401/04 |
| | | | | 514/235.2 |

FOREIGN PATENT DOCUMENTS

| WO | WO2010091233 | 8/2010 |
|---|---|---|
| WO | WO2012094658 | 1/2011 |
| WO | WO2012068545 | 5/2012 |

OTHER PUBLICATIONS

Rev Med Chil. May 2007;135(5):620-30. Epub Jul. 9, 2007. [Prevalence of severe sepsis in intensive care units. A national multicentric study]. Dougnac AL1, Mercado MF, Cornejo RR, Cariaga MV, Hernández GP, Andresen MH, Bugedo GT, Castillo LF; Grupo Chileno del Estudio de la Sepsis.

Crit Care. 2010;14(3):R85. doi: 10.1186/cc9014. Epub May 12, 2010 Urinary cystatin C is diagnostic of acute kidney injury and sepsis and predicts mortality in the intensive care unit, Nejat M1, Pickering JW, Walker RJ, Westhuyzen J, Shaw GM Frampton CM, Endre ZH.

Curr Opin Nephrol Hypertens. Jul. 2013;22(4):397-404. doi: 10.1097/MNH.0b013e32836213ee.FGF23 and Klotho in chronic kidney disease. Olauson H1, Larsson TE.

Am J Kidney Dis. Dec. 2009;54(6):1012-24. del: 10.1053/j.ajkd. 2009.07.020. Epub Oct. 21, 2009. Accuracy of neutrophil gelatinase-associated lipocalin (NGAL) in diagnosis and prognosis in acute kidney injury: a systematic review and meta-analysis. Haase M1, Bellomo R, Devarajan P, Schlattmann P, Haase-Fielitz A; NGAL, Meta-analysis Investigator Group.

Nat Rev Nephrol. Jun. 5, 2012;8(7):423-9. doi: 10.1038/nrneph. 2012.92. Klotho as a potential biomarker and therapy for acute kidney injury. Hu MC1, Moe OW.

Kidney Int. Dec. 1998;54(6):1817-31. Treatment of acute renal failure. Star RA1.

Blood Purif. 2014;37(4):271-85. doi: 10.1159/000360689. Epub Jul. 3, 2014. Neutrophil gelatinase-associated lipocalin: ready for routine clinical use? An international perspective, Ronco C1, Legrand M, Goldstein SL, Hur M, Tran N, Howell EC, Cantaluppi V, Cruz DN, Damman K, Bagshaw SM, Di Somma S, Lewington A.

Nephrol Dial Transplant. Feb. 2013;28(2):352-9. doi: 10.1093/ndt/gfs460. Epub Nov. 4, 2012. Secreted Klotho and FGF23 in chronic kidney disease Stage 1 to 5: a sequence suggested from a cross-sectional study. Pavik I1, Jaeger P, Ebner L, Wagner CA, Petzold K, Spichtig D, Poster D, Wüthrich RP, Russmann S, Serra AL.

ISR for PCT/CL2016/050056, Jan. 2, 2017, (3 pages).

Korean J Intern Med 2015; 30:489-495, Renal Klotho expression in patients with acute kidney injury, Min Young Seo.

Pediatr Nephrol DOI 10.1007/s00467-014-3006-1,2014, Fibroblast growth factor 23 and acute kidney injury, Javier A. Neyra.

Int J Clin Exp Med 2015;8(5):7351-7358, Klotho: a novel and early biomarker of acute kidney injury after cardiac valve replacement in adults, Yong-Jun Liu.

Torregrosa et al., Urinary Klotho measured by ELISA as an early biomarker of acute kidney injury in patients after cardiac surgery or coronary angiography, Nefrologia, 35(2), (2015), pp. 172-178.

Informe Pericial et al . . . , Mar. 8, 2017 (Examination Document for parent CL 201503047, includes search results).

Resquesta DelPerito . . . , Sep. 7, 2017 (Examination Document for parent CL 201503047, includes search results).

Guarda, E., et al., Gulas 2009 de la Sociedad Chilena de Cardiologla para el Tratamiento del Infarto Agudo del Miocardio con Supradesnivel del ST, Revista Chilena de Cardiologla, vol. 28, N°Feb. 2009, Artilculo Especial, pp. 223-254.

* cited by examiner

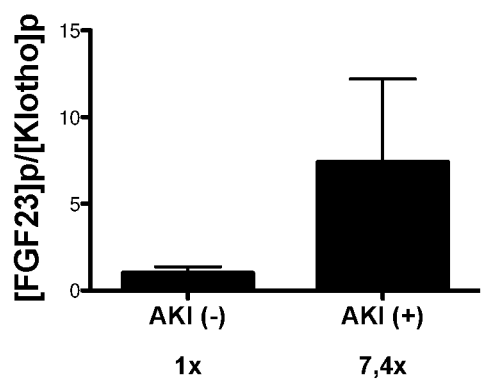
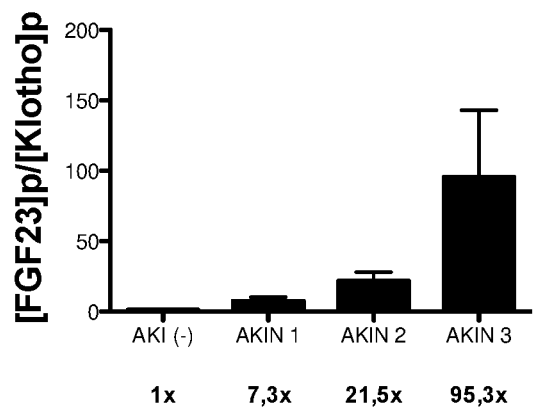
FIGURE 4M
FIGURE 4N
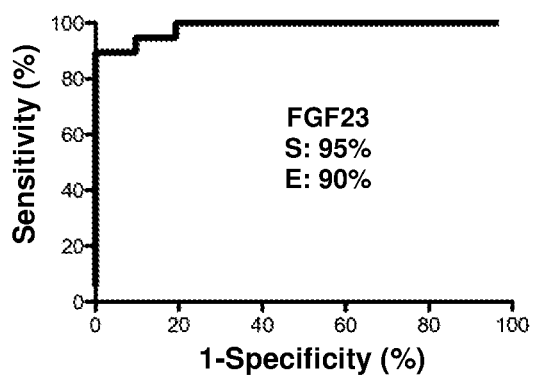
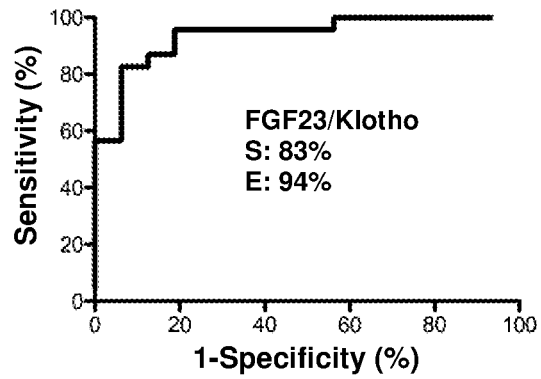
FIGURE 5A
FIGURE 5B
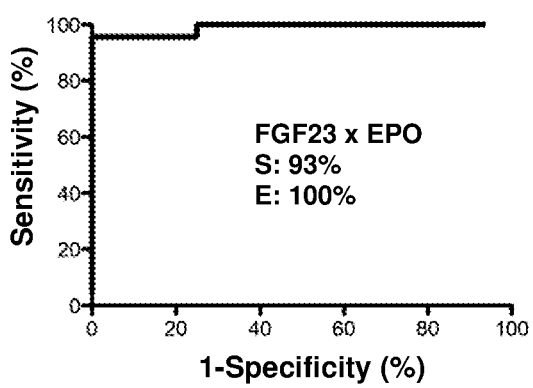
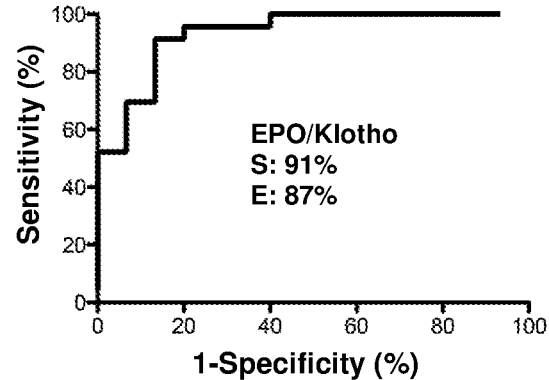
FIGURE 5C
FIGURE 5D

METHOD FOR THE EARLY DETECTION OF ACUTE KIDNEY INJURY IN CRITICAL PATIENTS, USING FIBROBLAST GROWTH FACTOR 23, KLOTHO AND ERYTHROPOIETIN AS BIOMARKERS

FIELD OF THE INVENTION

The present invention relates to the area of human health. In particular, a method to detect early acute kidney injury in critically ill patients which comprises using Fibroblast Growth Factor 23 (FGF23), Klotho (KL) and erythropoietin EPO) as biomarkers.

BACKGROUND

Acute Renal Injury (AKI) corresponds to the sharp drop observed primarily in hospitalized patients renal function. It is a condition of high morbidity and mortality in patients hospitalized in critical care units (ICU—Intensive Care Unit,.

The diagnosis of AKI is currently delayed when significant renal damage has developed, making difficult to recover renal function, in part due to the current lack of tools for early diagnosis.

The absence of early diagnosis has contributed to the absence of specific treatments, with consequent high morbidity and mortality in the short and long term.

Data from a Chilean study show that 1-year mortality in patients admitted to an ICU is 8% in patients without AKI, 22% in patients with AKI, and 42% in patients with AKIN 3, a severe form of AKI. See FIG. 1 (see Dougnac A. Rev Med Chile 2007 Guarda E. Rev Med Cardiol 2009 S. Melani Chilean Congress Nephrology 2012).

The present invention proposes a method using values obtained with the plasma concentration of 3 specific proteins, which together allow early detection (upon admission to the ICU) of AKI. The three selected proteins are: Erythropoietin (EPO), Klotho (KL) and Fibroblast Growth Factor 23 (FGF23).

The method of the present invention can be used to detect AKI in any patient, including a hospitalized patient with suspected AKI.

In the prior art, there are commercial kits for measuring the plasma concentration of these three proteins, without any existing kit to assess the 3 molecules together. Moreover, to date, these kits are not used in the study of AKI patients.

To date, there are no clinical practice of good biomarkers for the diagnosis of AKI, with ranges of sensitivity and specificity, and detection accuracy to be useful in the management of patients.

It has been reported that concentrations in urine, plasma and/or serum molecules as neutrophil gelatinase-associated lipocalin (NGAL), Cystatin C, Kidney Injury Molecule-1 (KIM-1), among others, increased in patients with AKI (Haase M Bellomo R, Devarajan P, P Schlattmann, Haase-Fielitz A. Accuracy of neutrophil gelatinase-associated lipocalcin (NGAL) in diagnosis and prognosis in acute kidney injury. a systematic review and meta-analysis Am J Kidney Dis 2009, 54: 1012-24 Nejat M.; Pickering J W, Walker R J, Westhuyzen J Shaw G M, Frampton C M, et al Urinary cystatin C is diagnostic of sepsis and acute Kidney Injury, and predicts mortality in the intensive care unit Crit Care 2010; 14 (3): R85; Parikh C R, Thiessen-Philbrook H, Garg A X, D Kadiyala, Shlipak M G, Koyner J L, et al Performance of kidney injury molecule-1 and liver fatty acid-binding protein and combined biomarkers of AKI after cardiac surgery Clin J Am Soc Nephrol 2013; 8 (7): 1079-1088). However, the performance of the determination of these proteins concentration to diagnose AKI in clinical practice is low, with high rates of false positives and false negatives. These problems limit their usefulness in the diagnosis and treatment of patients with AKI.

In fact, there are biomarkers of acute kidney injury in the market, including molecules with early rising in acute kidney injury (NGAL, KIM-1). However, these available biomarkers present low sensitivity/specificity for AKI diagnosis (60-85%). Furthermore, there is a delay in the range of hours to days in delivering the results of the determination of these proteins concentration.

To date, there are few studies on the use of biomarkers in real clinical conditions (most of them developing, Ronco C, Legrand M, Goldstein S L, Her M, Tran N, Howell E C, et al Neutrophil gelatinase-associated lipocalcin: ready for routine clinical use? purif An International Perspective Blood 2014; 37 (4): 271-85). One reason, as mentioned previously, is that the sensitivity/specificity found in clinical studies and meta-analyzes including a large numbers of patients have proven to be lower than originally proposed. For example, early studies of NGAL showed very high AUC, with clinical usefulness. However, studies of a hirer number of patients have shown that AUC is significantly lower in real conditions (Haase M, Bellomo R, Devarajan P, P Schlattmann, Haase-Fielitz A. Accuracy of neutrophil gelatinase-associated lipocalcin (NGAL) in diagnosis and prognosis in acute kidney injury: a systematic review and meta-analysis Am J Kidney Dis 2009; 54: 1012-1024). In addition, to date there is no clinical study of adequate quality to assess the usefulness of the biomarker in determining the use of a specific therapy for critically ill patients (Slew E D, Ware L B, Ikizler T A. Biological Markers of acute kidney injury. J Am Soc Nephrol 2011; 22: 810-20).

In the patent publication, US2011/0059537 A1, a method for determining whether a subject is at risk of AKI based on the detection of levels of at least two of the following molecules as indicators: MPO, PAI-1, MIP-1α, β MIP-1, EGF, MCP-1, G-CSF, FRACT, IL-2, IL-6, IL-10, IL-12, TNFa, sICAM and sVCAM is protected.

In patent publication WO2012068545 A1 a method to determine whether a subject is at risk of AKI based on the detection of urinary concentration of 2 proteins, NGAL and KIM-1, is protected.

In patent publication WO2012068545 A1 a method to determine whether a subject is at risk of AKI based on the detection of urinary concentration of 2 proteins, NGAL and KIM-1, is protected.

In patent publication US20140038203 A1 any increase in urine of 15 markers or the decrease of 1 from 4 markers for AKI detection is protected.

In the patent publication WO2012094658, methods and compositions for monitoring, diagnosis, prognosis, and determination of treatment regimens in subjects suffering from or suspected of having a kidney injury are disclosed. In particular, the invention relates to using a one or more assays configured to detect a kidney injury marker selected from the group consisting of Proheparin-binding EGF-like growth factor, Tenascin C, Angiopoietin-related protein 4, Fibroblast growth factor 19, Fibroblast growth factor 21 Heparin-binding growth factor 1. Angiopoietin-related protein 6, Proepiregulin, Probetacellulin Amphiregulin Angiogenin, Thrombospondin-2, and Collagen alpha-1 (XVIII) chain as diagnostic and prognostic biomarkers in renal injuries.

In the patent publication WO2010091233 the invention relates to methods and compositions for monitoring, diagnosis, prognosis, and determination of treatment regimens in subjects suffering from or suspected of having a renal injury. In particular, the invention relates to using assays that detect one or more markers selected from the group consisting of soluble advanced glycosylation end product-specific receptor, Bactericidal permeability-increasing protein, interleukin 12, Fibroblast growth factor 23, Vitamin K-dependent protein C, and Intestinal fatty acid-binding protein as diagnostic and prognostic biomarkers in renal injuries.

In the patent publication WO2010048347, the invention relates to methods and compositions for monitoring, diagnosis, prognosis, and determination of treatment regimens in subjects suffering from or suspected of having a renal injury. In particular, the invention relates to using assays that detect one or more markers selected from the group consisting of soluble CD44 antigen, Angiopoietin-1, soluble Angiopoietin-1 receptor, C-X-C chemokine motif 5, soluble Endoglin, soluble Tumor-associated calcium signal transducer 1, Erythropoietin, soluble Fractalkine, Heme oxygenase 1, soluble Interleukin-1 receptor type II, soluble Interleukin-6 receptor subunit-alpha, Lymphotactin, Lymphotoxin-alpha, Stromelysin-1, C-C motif chemokine 22, C-C motif chemokine 5, and Thrombospondin-1 as diagnostic and prognostic biomarkers in renal injuries.

The scientific publication of Current Opinion in Nephrology & Hypertension: July 2013-Volume 22-issue 4-p 397-404 "FGF23 and Klotho in chronic kidney disease" of Olauson, H et al, shows pathological changes. FGF23-Klotho in chronic kidney disease and suggests both molecules as clinical biomarkers that may provide novel strategies to alleviate cardiovascular risk and slow progression of chronic kidney disease.

In the scientific journal, "Secreted Klotho and FGF23 in chronic kidney disease Stage 1 to 5: a sequence Suggested from a cross-sectional study," Pavik I et al, received on Apr. 5, 2012 and accepted on Aug. 2, 2012, Oxford Journals Medicine & Health Nephrology Dialysis Transplantation, Volume 28, issue 2, pages 352-359, teaches that levels of Klotho and 1, 25-dihydroxy vitamin D3 (1, 25D) decreases linearly as the level of FGF23 increases early stages and the level of parathyroid hormone (PTH) is increased in later stages in chronic kidney disease.

In the scientific article, "FGF23-mediated regulation of systemic phosphate homeostasis: Klotho is an essential player?, M. Shawkat Razzaque, published in the American Journal of Physiology—Renal Physiology Published Mar. 1, 2009 Vol 296 no. 3, F470-F476 it is shown that the detection of circulating levels of FGF23 is an important tool for determining the causes of diseases associated with abnormal metabolism of metal ions. It also indicates that the pretreatment serum level of FGF23 is a good predictor of the effectiveness of vitamin D therapy in dialysis patients and that circulating levels of FGF23 can also be a useful marker for predicting the development of refractory hyperthyroidism (40). It is proposed that FGF23 is an important biomarker of early modality in patients with kidney disease, including patients whose levels of FGF23 are increased before developing hyperphosphatemia. It is suggested the value of FGF23 in diagnosis, prognosis and therapy. Similarly, compiled genetic evidence is provided on the in vivo relevance of Klotho to regulate systemic homeostasis of phosphate mediated by FGF23. Also, it is noted that the functions mediated FGF23 are mainly Klotho-dependent.

In the scientific journal, "Klotho and kidney disease." Chang Ming-H et al, (Available in PMC from Nov. 30 to Nov. 1, 2011. and published and J Nephrol. 2010 November-December; 23 (Supt 16): S136-S144) it is noted that Klotho is a very sensitive marker of damaged renal functions, and also that Klotho plays a pathogenic role in renal disease. In fact, it is indicated that Klotho is a key molecule in a variety of kidney diseases and has great potential as a biomarker for diagnosis and prognosis, as well as replacement therapy.

In the scientific article published in the journal Kidney International (2010) (volume 78, Number 1208 1210, "Klotho in acute kidney injury: biomarker, therapy, or a bit of Both?" By S Aiello et al.), it is mentioned that the diagnosis of acute kidney injury (AKI) is based on an increase in serum creatinine or a decrease in the amount of urine. However, the treatment of AKI to be effective should start very early after injury, long before the rise of creatinine concentration in serum. Thus, really sensitive biomarkers of tubular injury in AK are needed, and it is proposed that Klotho could be a biomarker and therapeutic target of ischemia induced AKI.

In the scientific article published in the journal Nature Reviews Nephrology (volume 8, 423-429, July 2012), "Klotho as a potential biomarker and therapy for acute kidney injury" Ming-Chang Hu & Orson W. Moe indicated that Klotho is a single-pass transmembrane protein that is strongly expressed in the kidneys, which is known as co-receptor protein for the Fibroblast Growth Factor 23. Further, it is indicated that Klotho deficiency is an early event in acute kidney injury (AK) and a pathogenic factor exacerbating the acute renal damage that contributes to long-term results. Recovery by exogenous supplementation or stimulation of endogenous Klotho can prevent or minimize injury, promoting recovery and suppressing fibrosis for the amelioration of the development of chronic kidney disease. Then, it is proposed to Klotho as a highly promising candidate either as a biomarker or therapeutic agent for AKI.

On the basis of this evidence, it is clear that although there have been disclosed various methods for detection of AKI, or renal diseases none of these documents communicates the measurement and the measurement of the three molecules together (plasma concentration), of the three markers proposed in the present invention.

As shown, the examples included below, the method of the present invention is potentially superior because FGF23, Klotho and EPO have demonstrated an early increase, with high-sensitivity (close to 100%), with an accuracy better than 90% for AKI detection.

The examples also demonstrate that the measurements of plasma concentration of FGF23, Klotho and EPO are prognostic predictors of patients mortality. Patients with elevated levels of FGF23 or decreased Klotho levels have increased 30 day mortality versus those with levels in the normal range (mortality 22% vs. 0%). This performance has not been observed in any of the other biomarkers studied to date.

In the examples section, we provide data demonstrating that plasma levels of FGF23, EPO and Klotho are predictors for AKI detection, for AK severity and for risk of death of the patient. The performance of the measurement of the three biomarkers taken together is superior to the performance of those biomarkers available today.

Thus, the method of the present invention provides a method of early detection and follow up, based on the joint use of the measurements of the three specific biomarkers, FGF23, EPO and Klotho, involving the measurement of changes in plasma and/or urinary concentration of the three proteins mentioned, from a blood sample, or alternatively, from a urine sample.

BRIEF DESCRIPTION OF THE FIGURES

FIGS. 5A-5E shows the ROC curve, sensitivity and specificity of FGF23 (A), FGF23/Klotho (B), FGF23×EPO (C), EPO/Klotho (D) and FGF23×EPO/Klotho (E) to detect the presence/development of AKI in critically ill patients, at the admission to the Intensive Care Unit.

DETAILED DESCRIPTION OF THE INVENTION

For example, the ex vivo method of the present invention can be applied in critically ill patients admitted to the ICU due to severe disease (severe infections, severe burns, post highly complex surgeries, cerebral infarction, etc.). These patients are subjected to extraction of venous blood samples The extraction of blood samples is performed by a standard procedure applicable to this type of patient, then the sample will be carried to a clinical or research laboratory, where the extraction of plasma will be performed. Thus, samples can be analyzed by ELISA technique (their acronym, Enzyme-Linked ImmunoSorbent Assay) for the determination of plasma levels of FGF23, Klotho and Erythropoietin. Levels that may be available during the first hours after the admission of the patient.

Plasma levels (here in after referred to only as levels) thus obtained are incorporated in the following indicators to determinate the probability to develop AKI:

Indicators:
1=$([FGF23]_p \times [EPO]_p)$
2=$([FGF23]_p / [Klotho]_p)$
3=$([EPO]_p / [Klotho]_p)$
4=$(([FGF23]_p \times [EPO]_p) / [Klotho])_p)$ where $[X]_p$ is defined as the plasma level of a specific molecule (X), which includes fibroblast growth factor 23 (FGF23), Klotho and Erythropoietin (EPO).

If the indicator value 1, 2, 3, 4 or two or more thereof, is higher or equal to a cut-off point (10U) that, there is a high probability of presence/development of AKI, which may allow to perform specific therapies for the management/ prevention of AKI. If the indicator value 1, 2, 3, 4 or two or more of thereof is lower than the cut-off point, the probability of presence/development of AKI is low and patients would only require standard therapies.

Figure 1:
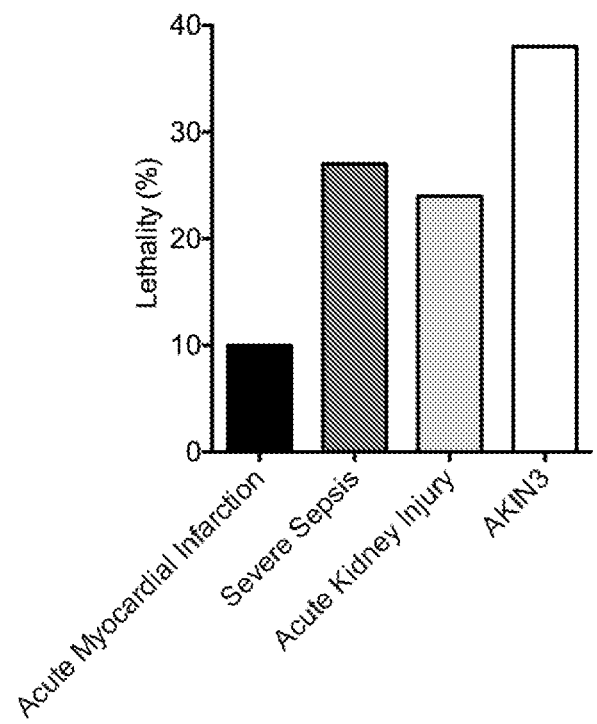
FIG. 1 shows the average lethality of AKI (as average) and AKIN3 (severe form), compared to other conditions of high morbidity and mortality such as sepsis (severe infection) and myocardial infarction (AMI).
Figure 2:
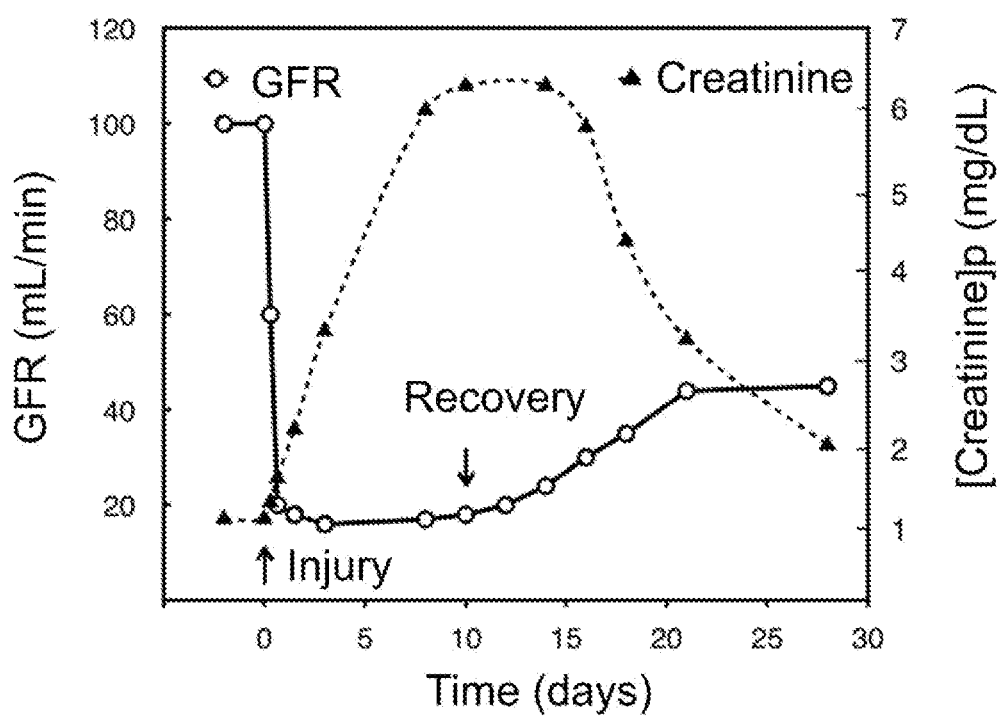
FIG. 2 shows the delayed response increase creatinine (current method to detect AKI), as compared to the decrease in renal function (GFR). (Adapted from: Star RA Treatment of acute renal failure Kidney Int 1998; 54: 1817-1831
Figure 3:
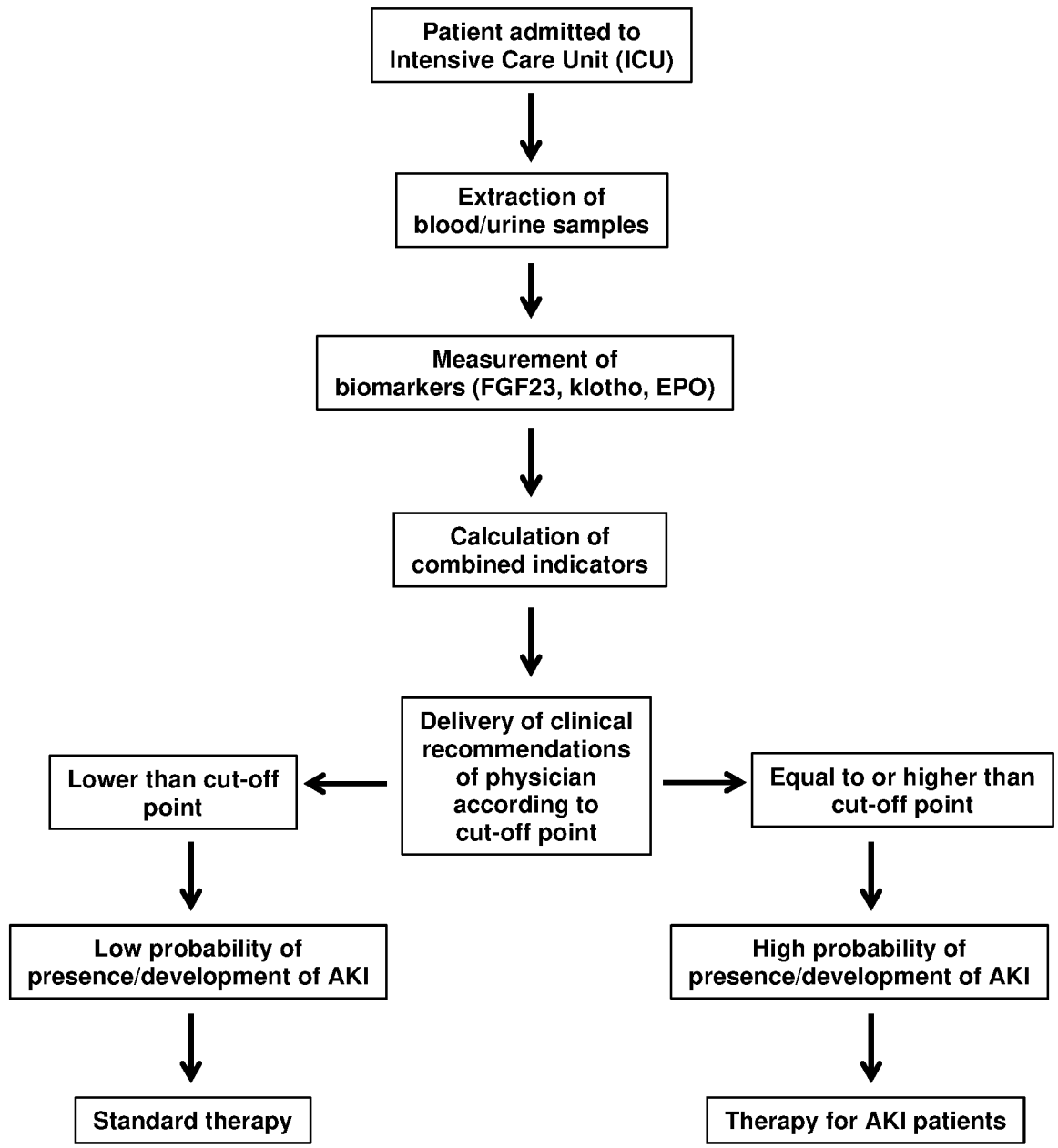
FIG. 3 shows an algorithm for the measurement and implementation of the present invention. Briefly, in patients admitted to ICU blood and urine samples will be obtained for measurement of biomarkers (FGF23, Klotho, EPO) and calculation of combined indicators. Then, according to the results, the risk of the presence/development of AKI will be calculated, and according to this risk, specific clinical recommendations will be delivered to the physician responsible of the patient.
Figure 4A:
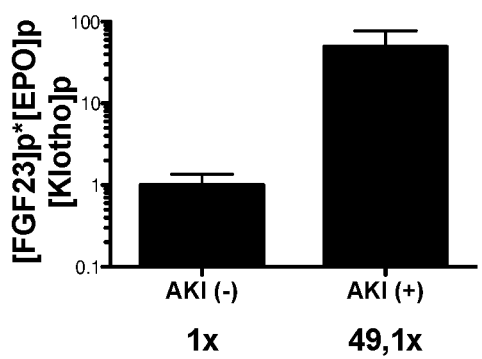
FIGS. 4A-4N shows the results of the measurements of plasma levels of FGF23×EPO/Klotho (A-B), FGF23 (C-D), EPO (E-F), Klotho (G-H), EPO/Klotho FGF23×EPO (K-L) and EPO/Klotho (M-N), according to the presence/absence of AKI, and severity of AKI. These data shows that the combined parameters increase significantly in patients with AKI, with an increase proportionally to the severity of renal injury.
Figure 4B:
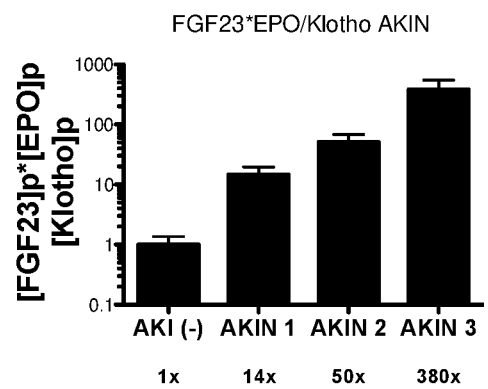
Figure 4C:
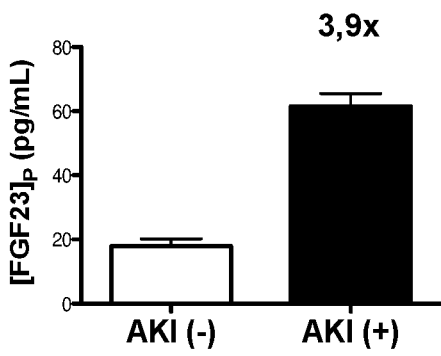
Figure 4D:
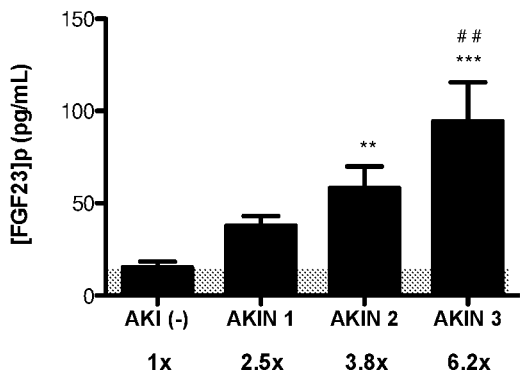
Figure 4E:
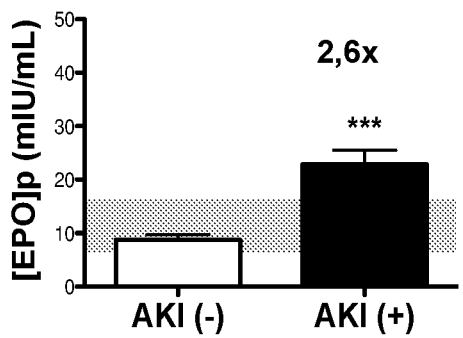
Figure 4F:
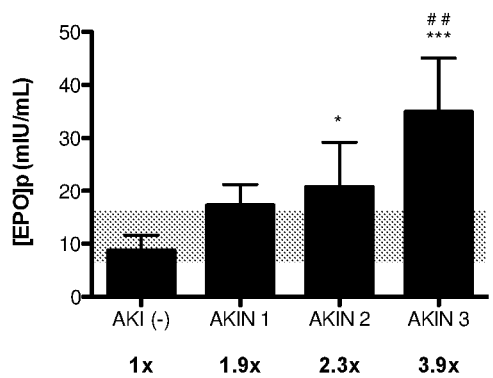
Figure 4G:
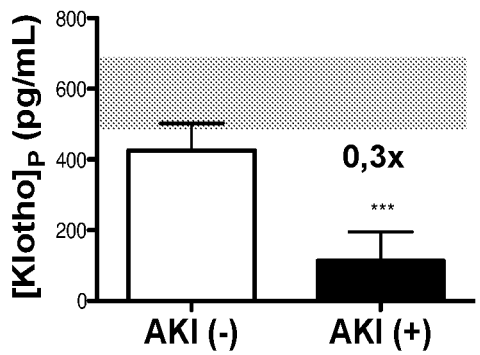
Figure 4H:
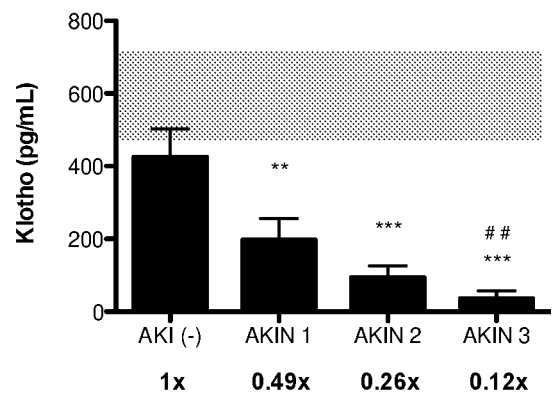
Figure 4I:
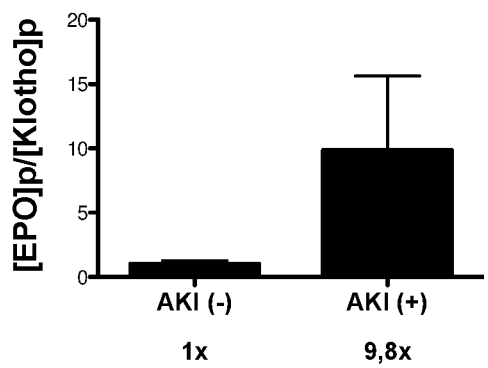
Figure 4J:
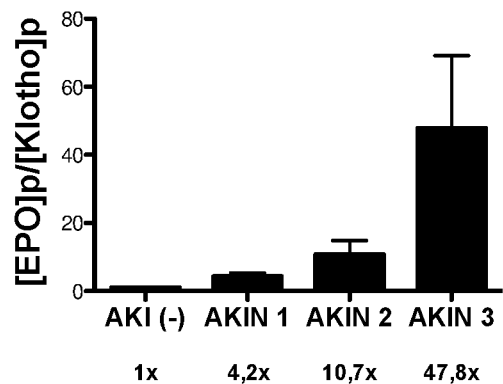
Figure 4K:
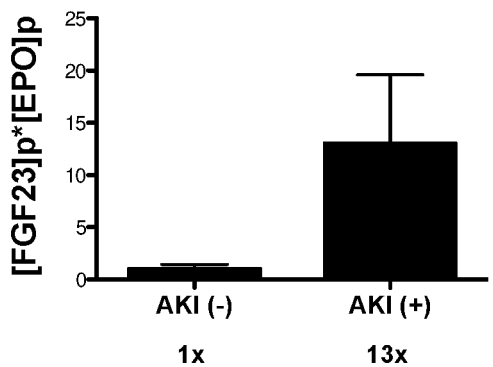
Figure 4L:
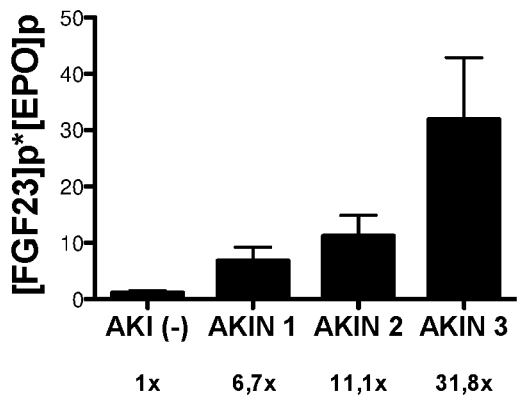
Figure 5E:
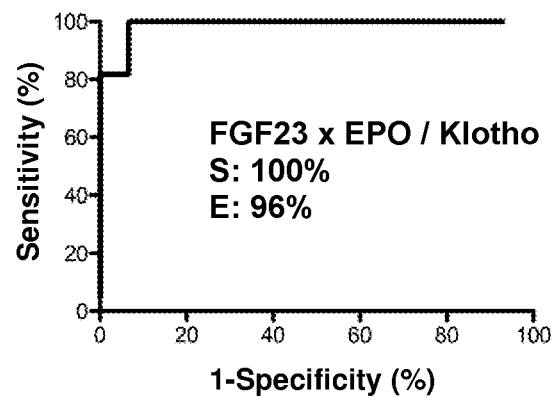

FIGS. 5A-5N show ROC analysis (their acronym, Receiver Operating Characteristic) obtained by the inventors, which determines the sensitivity and specificity of the indicators. These results show that combined parameters have high sensitivity and specificity to predict the presence/ development of AKI.

Figure 6:
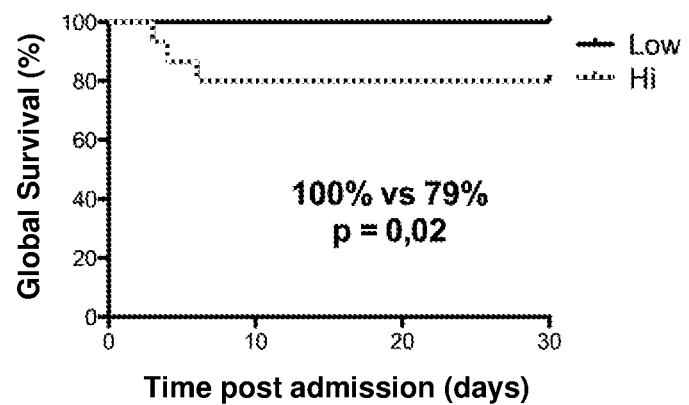
FIG. 6 shows the global survival curve of critically ill patients with sepsis, stratified with high or low levels of the combined parameter during the first 30 days of hospital admission. We found that high levels of the combined parameter are associated to increased 30-day mortality.

The combined parameters also determine whether the patient has a high or low probability to require vasoactive drugs (medications given to patients with very low blood pressure to normalize it) or dialysis during the hospitalization. Also, survival analysis indicate that patients with high levels of the combiner parameter have increased mortality compared to those with lower levels, as represented in Kaplan-Meier analysis (FIG. 6).

This data would be available during the early hours of the patient, so that could be defined in advance, the measures to take to prevent the development of kidney damage in patients with high risk of presence/development of AKI.

In the following section, we present 3 examples where the parameter could be useful.

EXAMPLE 1

Patient Characteristics: Patient admitted to the critical care unit coming from the emergency department or hospitalized in a non-critical unit, with a diagnosis of severe sepsis/septic shock, polytrauma or acute coronary syndrome (conditions with increased risk to develop AKI).

Sampling time: Upon entry of hospital, a sample of venous blood and urine is taken.

Sample processing: Plasma extraction and measurement of the concentration of FGF23, Klotho and Erythropoietin, to obtain results in a few hours Analysis of results: Determination of plasma levels and results of combined indicators, that is, 1=(FG23 value×EPO value), 2=(FGF23 value/Klotho value), 3=(EPO value/ Klotho value) and 4=((FGF23 value×EPO value)/Klotho value). The result would be used to determinate a treatment recommendation, based in the indicator value (greater or less than 10U).

Possible actions: 1) less than 10U (cutoff) value indicator: Maintain standard therapy without adding crystalloid solutions without restriction potentially nephrotoxic drugs. 2) greater or equal than 10U indicator value: Maintain standard therapy, add crystalloid solutions, restrict use of potentially nephrotoxic drugs, and optionally, making early emergency dialysis.

Reevaluation of patient: Extraction of blood samples at 24 and 48 hours, with reassessment of the value of the indicator and redefine behaviors to follow.

EXAMPLE 2

Patient Characteristics: Patient hospitalized in a noncritical unit, with diagnosis of severe sepsis, heart failure, liver failure, chronic kidney disease, coming from Emergency Service Sampling time: At admission to hospital, an extraction of venous blood and urine samples will be performed.

Sample processing: Plasma extraction and measurement of the concentration of FGF23, Klotho and Erythropoietin, to obtain results in a few hours.

Analysis of results: Determination of plasma levels and results of combined indicators, that is, 1=(FGF23 value×

EPO value), 2=(FGF23 value/Klotho value), 3=(EPO value/Klotho value) and 4=((FGF23 value×EPO value)/Klotho value). The result would be used to determinate a treatment recommendation, based in the indicator value (greater or less than 10U).

Possible actions: 1) less than 10U (cutoff) value indicator: Maintain standard therapy without adding crystalloid solutions without restriction potentially nephrotoxic drugs. 2) greater or equal than 10U indicator value: Consider transfer to critical care unit likely given poor medical evolution, add crystalloid solutions, restrict use of potentially nephrotoxic drugs, and optionally, making early emergency dialysis.

Reevaluation of patient: Extraction of blood samples at 24 and 48 hours, with reassessment of the value of the indicator and redefine behaviors to follow.

EXAMPLE 3

Patient Characteristics: Patient admitted to the Intensive Care Unit after medium or high complexity surgery (heart surgery, vascular surgery, abdominal surgery, neurosurgery). Sampling time: After admission of ICU, a sample of venous blood and urine is taken.

Patient Characteristics: Patient admitted to the Intensive Care Unit after medium or high complexity surgery (heart surgery, vascular surgery, abdominal surgery, neurosurgery). Sampling time: After admission of ICU, a sample of venous blood and urine is taken.

Analysis of results: Determination of plasma levels and results of combined indicators, as mentioned in Example 1. The result would be used to determinate a treatment recommendation, based in the indicator value (greater or less than 10U.

Possible actions: 1) Lower than breakpoint indicator value: Maintain standard therapy without adding crystalloid solutions without restriction potentially nephrotoxic drugs. 2) Higher or equal than cutoff indicator value: Maintain standard therapy, add crystalloid solutions, restrict use of potentially nephrotoxic drugs, and optionally, making early emergency dialysis.

Reevaluation of patient: Taking further blood samples at 24 and 48 hours, with reassessment of the value of the indicator and redefine behaviors to follow.

We claim:

1. A method for diagnosing and treating early acute kidney injury (AKI), the method comprising:
   a) obtaining at least one plasma sample from a patient;
   b) performing an immunoassay on the at least one plasma sample to determine the levels of fibroblast growth factor 23 (FGF23), Klotho and Erythropoietin (EPO);
   c) calculating an indicator value, wherein the indicator value is determined by the equation $((FGF23_p \times EPO_p)/Klotho_p)$ wherein $FGF23_p$ is the plasma level of FGF23, $EPO_p$ is the plasma level of EPO, and $Klotho_p$ is the plasma level of Klotho;
   d) determining said patient has AKI when the indicator value is equal to or higher than a cut-off point of 10-U; and
   e) treating the patient determined to have AKI by administering crystalloid solutions and restricting the patient's use of nephrotoxic drugs.

2. The method of claim 1, wherein treating at step e) further includes administering early emergency dialysis.

* * * * *